(12) United States Patent
Hayashi (10) Patent No.: US 7,741,047 B2
(45) Date of Patent: Jun. 22, 2010

(54) METHOD FOR TREATING AUTOIMMUNE DISEASES AND SCREENING METHOD FOR PREVENTIVE OR THERAPEUTIC AGENT FOR THE SAME

(75) Inventor: Yoshio Hayashi, Tokushima (JP)

(73) Assignee: Kowa Co., Ltd., Nagoya-shi (JP)

( * ) Notice: Subject to any disclaimer, the term of this patent is extended or adjusted under 35 U.S.C. 154(b) by 0 days.

(21) Appl. No.: 11/967,599

(22) Filed: Dec. 31, 2007

(65) Prior Publication Data

US 2008/0213776 A1    Sep. 4, 2008

Related U.S. Application Data

(62) Division of application No. 11/589,838, filed on Oct. 31, 2006, now abandoned, which is a division of application No. 10/685,448, filed on Oct. 16, 2003, now abandoned.

(30) Foreign Application Priority Data

Apr. 28, 2003    (JP)    ............... 2003-123959

(51) Int. Cl.
C12Q 1/68    (2006.01)
G01N 33/53    (2006.01)

(52) U.S. Cl. ............................ 435/6; 435/7.1

(58) Field of Classification Search ............... None
See application file for complete search history.

(56) References Cited

U.S. PATENT DOCUMENTS 4,281,061 A    7/1981    Zuk et al.

OTHER PUBLICATIONS

Ishimaru et al., 2008, J. Exp. Med. vol. 205: 2915-2927.*
Naozumi Ishimaru, et al., "Identification of Estrogen-Related Factors Relating to the Onset Mechanism of Sjogren's Syndrome and Analysis of the Factors", Proceedings of Annual Meeting of the Japanese Society for Immunology, vol. 32, 2002, (18 pgs.) (with partial English translation, pp. 1-4).
Petition filed May 21, 2003 to the Commissioner, the Patent Office of Japanese Application No. 2003-123959, with accompanying English translation (3 pages) of the Japanese Declaration (3 pages).
N. Ishimaru, et al., American Journal of Pathology, vol. 155, No. 1, pp. 173-181, "Estrogen Deficiency Accelarates Autoimmune Exocrinopathy in Murine Sjogren's Syndrome Through Fas-Metitated Apoptosis", Jul. 1999.
Y-W. Qian, et al., Nature, vol. 364, pp. 648-652, "A Retinoblastoma-Binding Protein Related to a Negative Regulator of Ras in Yeast," Aug. 12, 1993.
Y-W. Qian, et al., The Journal of Biological Chemistry, vol. 270, No. 43, pp. 25507-25513, "Dual Retinoblastome-Binding Proteins With Properties Related to a Negative Regulator of Ras in Yeast," Oct. 27, 1995.
E. Nicolas, et al., The Journal of Biological Chemistry, vol. 275, No. 13, pp. 9797-9804, "RbA$_p$48 Belongs to the Histone Deacetylase Complex That Associates With the Retinoblastoma Protein," Mar. 31, 2000.
Ishimaru, et al., 2006, Mol. Cell. Biol. vol. 26: 2924-2935.
Clayton, 2004, Nature, vol. 430, pp. 599-605.
Ishimaru et al., 2003, Am. J. Pathol., vol. 163, pp. 1481-1490.
Nakamura et al., 2006, Translational Research, vol. 148, pp. 281-288.
Rosen, et al., 2004, Crit. Rev. Oral., Biol. Med., vol. 15, pp. 156-164.
Kong, et al., 2007, J. Biol. Chem., In press article, pp. 1-29.

* cited by examiner

*Primary Examiner*—Amy E Juedes
(74) *Attorney, Agent, or Firm*—Oblon, Spivak, McClelland, Maier & Neustadt, L.L.P.

(57) ABSTRACT

The present invention is directed to a method for treating autoimmune diseases comprising administering RBAp48 production suppressor or inhibitor; a screening method for a preventive or therapeutic agent for autoimmune diseases comprising determining RBAp48 production suppressing effect or inhibitory effect of a sample; a diagnosis agent or a diagnosing kit for autoimmune diseases containing a reagent for measuring RBAp48 level in gland tissue; and a diagnosis method for autoimmune diseases comprising measuring RBAp48 level in gland tissue.

4 Claims, 6 Drawing Sheets

METHOD FOR TREATING AUTOIMMUNE DISEASES AND SCREENING METHOD FOR PREVENTIVE OR THERAPEUTIC AGENT FOR THE SAME

CROSS-REFERENCE TO RELATED APPLICATIONS

This application is a divisional of U.S. Ser. No. 11/589,838, filed on Oct. 31, 2006, which is a divisional of U.S. Ser. No. 10/685,448, filed on Oct. 16, 2003, which claims priority to JP 2003-123959, filed on Apr. 28, 2003.

BACKGROUND OF THE INVENTION

1. Field of the Invention

The present invention relates to a method for treating autoimmune diseases, a screening method for a preventive or therapeutic agent for autoimmune diseases, and a diagnostic method for autoimmune diseases.

2. Background Art

Autoimmune diseases are pathological conditions caused by antibodies (autoantibodies) which are formed against components that constitute an individual's own body (autoantigens), or by T cells formed against such autoantigens. Various types of autoimmune diseases have been known: Some affect specific organs, and some others develop systemically. Autoantibodies provide a broad range of actions. Specifically, autoantibodies destruct cells (as in, e.g., autoimmune hemolytic anemia); impair physiological functions (as in, e.g., myasthernia gravis); excessively stimulate receptors (as in, e.g., Basedow's disease (Graves' disease)); or form antigen-antibody complexes (immune complexes) as deposits on the walls of blood vessels, to thereby cause inflammation (as in, e.g., systemic lupus erythematosus (SLE)). Usually, an individual does not immunologically respond to its own antigens; i.e., autoantigens (this mechanism is called self tolerance). However, according to current theory, when the self tolerance is lost for some reason, the individual develops an autoimmune disease. General causes of autoimmune diseases have not been elucidated. Therefore, symptomatic approaches have been major measures for treatment of autoimmune diseases, and practically, there is no well-established therapeutic method as yet.

Among other autoimmune disease, Sjögren's syndrome has been known to cause systematic chronic inflammation in exocrine glands of the whole body, including the lacrimal glands and the salivary glands, and which primarily involves dryness caused by functional deterioration of exocrine glands, as found in, for example, sicca syndrome associated with keratoconjunctivitis sicca or chronic sialadenitis. In addition to some hereditary factors, other factors such as immune disorders and unknown environmental factors are also believed to contribute to Sjögren's syndrome. However, details remain unknown, and thus, a need continues to exist for a radical, course-specific therapeutic method.

In one approach to elucidating the pathological causes of autoimmune diseases, researchers focus on the fact that most autoimmune diseases, including Sjögren's syndrome, develop primarily in menopausal or postmenopausal women. This suggests that estrogen deficiency causes some change in the target organs. In search for supportive evidence, the present inventor performed studies through use of mice suffering Sjögren's syndrome and reported that estrogen deficiency causes apoptosis of gland cells to thereby aggravate pathological conditions, and that through administration of estrogen, aggravation of the pathological conditions can be prevented (Ishimaru N, et al. *Estrogen deficiency accelerates autoimmune exocrinopathy in murine Sjogren's syndrome through fas-mediated apoptosis*, Am. J. Pathol. 155 (1), 173-81 (1999)).

RBAp48 (retinoblastoma associated protein 48) is a nucleoprotein which forms a complex with Rb protein (a known tumor suppressor gene product). Human RBAp48 gene was first obtained in 1993 (Qian Y W, et al. *A retinoblastoma-binding protein related to a negative regulator of Ras in yeast*, Nature 364 (6438), 648-52 (1993)). RBAp48 has been reported to form histone deacetylase complex to thereby participate in regulating cell differentiation or cell multiplication (Qian Y W, et al. *Dual retinoblastoma-binding proteins with properties related to a negative regulator of ras in yeast*, J. Biol. Chem. 270 (43), 25507-13 (1995); Nicolas E., et al. *RBAp48 belongs to the histone deacetylase complex that associates with the retinoblastoma protein*, J. Biol. Chem. 275 (13), 9797-804 (2000)). However, nothing has been known in relation to what effect RBAp48 exerts on improvement of pathological conditions of patients who suffer autoimmune diseases.

Accordingly, the present invention is directed to a method for treating autoimmune diseases, for which radical therapies have not yet been obtained; to a screening method for preventive or therapeutic agents for autoimmune diseases; and to a diagnostic method for autoimmune diseases.

SUMMARY OF THE INVENTION

In view of the foregoing, the present inventor has performed extensive studies and confirmed that RBAp48 is one factor that is expressed in cells of the salivary glands—a target organ of autoimmune diseases, particularly Sjögren's syndrome—when estrogen is deficient, and that apoptosis of the salivary gland cells is induced by incorporating RBAp48 into the cells. On the basis of these findings, the present inventors have found that autoimmune diseases can be diagnosed by determining RBAp48 level in gland tissues; screening of candidate preventive or therapeutic agents for autoimmune diseases can be performed through determination of the RBAp48 production suppressing effect or RBAp48 production inhibitory effect of a sample; and an RBAp48 production suppressor or inhibitor exhibits excellent preventive or therapeutic effect on autoimmune diseases such as Sjögren's syndrome and thus is useful as a drug for autoimmune diseases, thereby leading to completion of the present invention.

Accordingly, the present invention provides a method for treating autoimmune diseases comprising administering RBAp48 production suppressor or inhibitor; a screening method for a preventive or therapeutic agent for autoimmune diseases comprising measuring the RBAp48 production suppressing effect or inhibitory effect of a sample; a diagnostic agent or a diagnosing kit for autoimmune diseases containing a reagent for measuring the RBAp48 level in gland tissue; and a diagnostic method for autoimmune diseases comprising measuring the RBAp48 level in gland tissue.

BRIEF DESCRIPTION OF THE DRAWINGS

Various other objects and features and many of the attendant advantages of the present invention will be readily appreciated as the same becomes better understood by reference to the following detailed description of the preferred embodiments when considered in connection with the accompanying drawings, in which.

DETAILED DESCRIPTION OF PREFERRED EMBODIMENTS

All the documents referred to in the present specification are incorporated herein by reference.

No particular limitations are imposed on the RBAp48 production suppressor or inhibitor; i.e., the effective agent employed in the method for treating autoimmune diseases of the present invention, so long as the suppressor or inhibitor inhibits the function of RBAp48. Examples of the suppressor or inhibitor include RBAp48 gene antisense oligonucleotide; agents which inhibit RBAp48 gene expression by, for example, inhibiting RBAp48-specific transcription factor; agents which decompose specifically RBAp48 mRNA by, for example, RNA interference action of double-strand RNAs; agents which inhibit RBAp48 protein expression; agents which inhibit post-expression modification of RBAp48; and agents which inhibit the function of RBAp48 such as RBAp48 functional antibody.

When an autoimmune disease is treated, the dose, administration site, administration interval, administration term, etc. of the drug are determined in accordance with, for example, the sex, age, body weight, and pathological conditions of the patient to which the drug is administered; other drugs which may be administered in combination with the drug; and type of the therapeutic method. The RBAp48 production suppressor or inhibitor, which is the effective agent employed in the present invention, may be used singly or in combination with a pharmacologically acceptable carrier, such as a solubilizing agent, an excipient, a binder, or a diluent. No particular limitations are imposed on the dosage form of the drug employed in treating autoimmune diseases according to the present invention, and examples of the dosage form include tablets, capsules, granules, powder, lotion, plaster, injection, and suppository. These drug preparations may be produced through known methods. For example, an oral drug preparation may be produced through processing the effective agent with, among others, a solubilizing agent such as tragacanth gum, acacia, a sucrose ester, lecithin, olive oil, soybean oil, or PEG400; an excipient such as starch, mannitol, or lactose; a binder such as sodium carboxymethylcellulose or hydroxypropylcellulose; a disintegrant such as crystalline cellulose or calcium carboxymethylcellulose; a lubricant such as talc or magnesium stearate; or a flowability-improving agent such as light anhydrous silicic acid, which are suitably selected.

In the method for treating autoimmune diseases of the present invention, the effective agent is administered perorally or perenterally. The dose of the effective agent differs depending on the patient's body weight, age, sex, medical conditions, etc. The daily dose of the effective agent for an adult is typically 0.01 to 1,000 mg, preferably 0.1 to 100 mg. The effective agent is preferably administered once a day, or several times a day in a divided manner.

The method for treating autoimmune diseases of the present invention can be applied to various autoimmune diseases. Examples of the autoimmune diseases include Hashimoto's thyroiditis, SLE, Goodpasture's syndrome, pemphigus, receptor autoimmune diseases, Basedow's disease (Graves' disease), myasthernia gravis, insulin resistant diseases, autoimmune hemolytic anemia, autoimmune thrombocytopenic purpura, autoimmune encephalomyelitis, rheumatism, scleroderma, mixed connective tissue disease, polymyositis, pernicious anemia, idiopathic Addison's disease, some types of infertility, glomerulonephritis, bullous pemphigus, Sjögren's syndrome, some types of diabetes, adrenergic agent resistance, chronic active hepatitis, primary biliary cirrhosis, endocrine failure, vitiligo, angiitis, post-cardiac surgery syndrome, urticaria, atopic dermatitis, some types of asthma, and inflammatory, granulomatous, denatured, or atrophic diseases having unknown causes.

In the screening method for a preventive or therapeutic agent for autoimmune diseases, RBAp48 production suppression effect or RBAp48 production inhibitory effect may be determined through a method known per se. For example, there may be used a reaction in which RBAp48 gene is transferred into a gland cell (e.g., human salivary gland cell), to thereby enhance RBAp48 productivity of the cell, inducing apoptosis of the cell. When a sample agent has been added to the cell in advance, if apoptosis is suppressed, the sample agent is determined to be useful as a preventive or therapeutic agent for autoimmune diseases. Whether or not a sample agent has RBAp48 production suppression effect or inhibitory effect may be determined through measuring apoptosis of the cells having enhanced RBAp48 productivity, but it can also be determined through measuring RBAp48 gene in such cells or through directly measuring RBAp48 itself in such cells. Of course, the testing system as described above may be used in screening out a substance having apoptosis inhibitory effect.

In the diagnostic method for autoimmune diseases of the present invention, the RBAp48 level or RBAp48 gene expression in gland tissues is determined through a known method. The RBAp48 level is determined preferably through an immunological assay, more preferably through ELISA.

Examples of the assay for determining RBAp48 gene expression include PCR, northern blotting, and microarray assays. Examples of the gland tissue include salivary gland, lacrimal gland, thyroid, exocrine pancreas, intrahepatic bile duct, sweat gland, mammary gland, harderian gland, prostate gland, and bulbourethral gland. These tissues may be collected from subjects through, for example, biopsy or autopsy. The assay may be applied for samples other than gland tissues. Examples of such samples include serum, saliva, tear, bile, pancreatic juice, cerebrospinal fluid, and urine which are collected from subjects. The present invention can also be performed through determining, for example, RBAp48 or an RBAp48-related factor (e.g., a binding protein, an antibody, an inducible protein, and a denatured protein) in the sample.

No particular limitations are imposed on the diagnostic agent for autoimmune diseases of the present invention, so long as the agent contains a reagent which can be used to determine the RBAp48 level in the gland tissue. Examples of the reagent to be used in immunological assays include reagents containing an anti-RBAp48 monoclonal antibody and reagents containing an anti-RBAp48 polyclonal antibody. Preferably, the diagnosis agent further contains a labeled substance such as a labeled secondary antibody, a labeled anti-RBAp48 monoclonal antibody, or a labeled anti-RBAp48 polyclonal antibody. Examples of the labeling substance include a radioisotope, an enzyme, a fluorescent substance, and a luminescent substance.

EXAMPLES

The present invention will next be described in detail by way of examples, which should not be construed as limiting the invention thereto.

Example 1

Apoptosis of Salivary Gland Cells of Normal Mice

Figure 1:
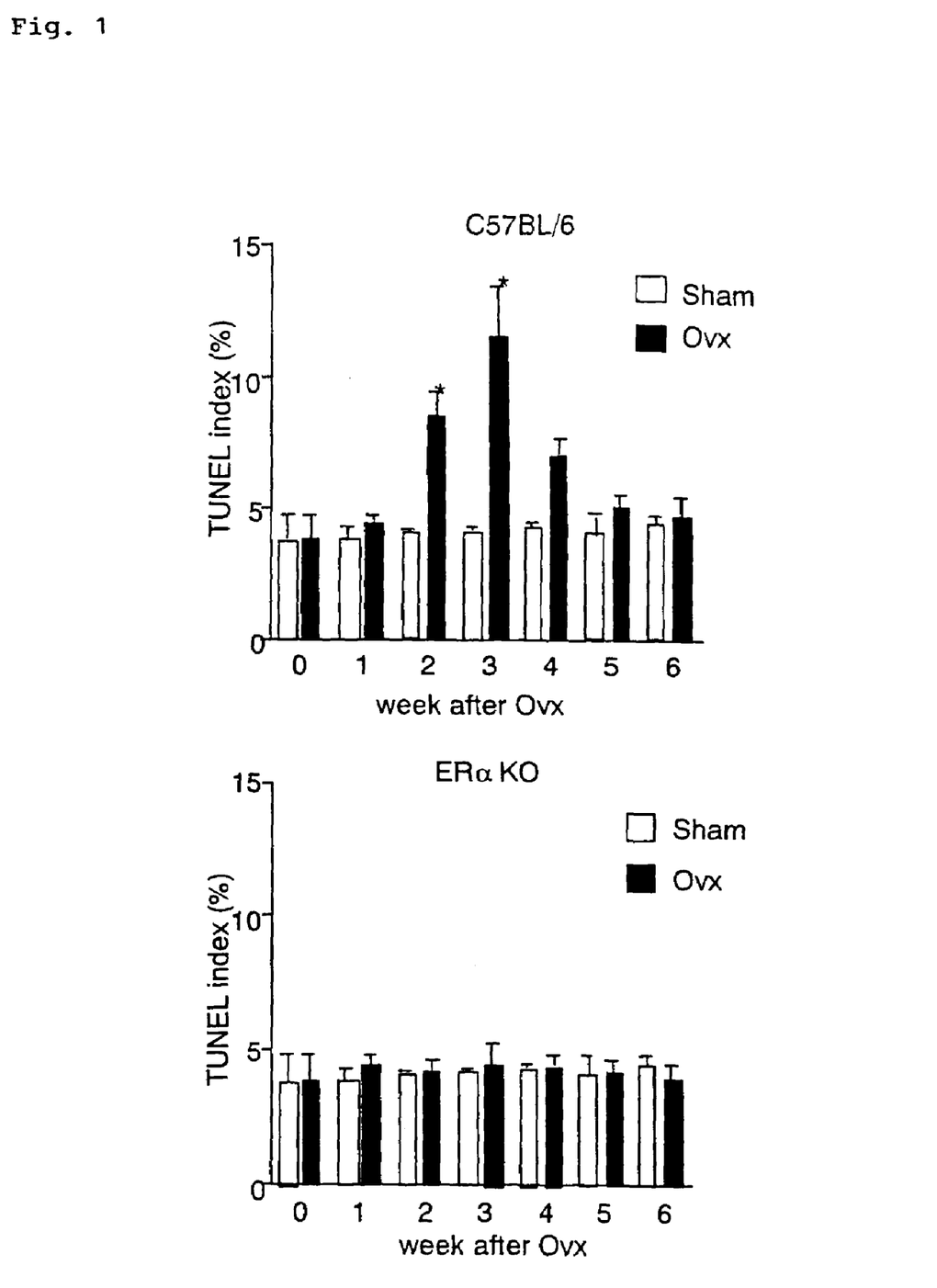
FIG. 1 is a graph showing apoptosis of salivary gland cells of normal mice, wherein "TUNEL index" represents stain index, "Ovx" represents groups on which ovariectomy has been performed, "Sham" represents groups on which sham operation has been performed, and "week after Ovx" represents weeks after the ovariectomy was performed.

C57BL/6 mice and estrogen receptor knockout (ERαKO) mice were ovariectomized (Ovx), and salivary gland cells of each mouse were observed over time for six weeks after the ovariectomy in terms of apoptosis. Slices of the salivary gland cells were stained through TUNEL, and whether or not apoptosis occurred was evaluated from the stain index (TUNEL index). Sham operation groups (Sham), to which Ovx had not been performed, were used as controls. As a result, as shown in FIG. 1, transient apoptosis was observed from two to three weeks after Ovx in the salivary gland cells of the C57BL/6 mice to which ovariectomy had been performed. In contrast, in the salivary gland cells of the ERαKO mice, increase in apoptotic cells was not observed. Thus, apoptosis of salivary gland cells was confirmed to involve estrogen deficiency.

Example 2

Apoptosis Induction of Cultured Cells

Figure 2:
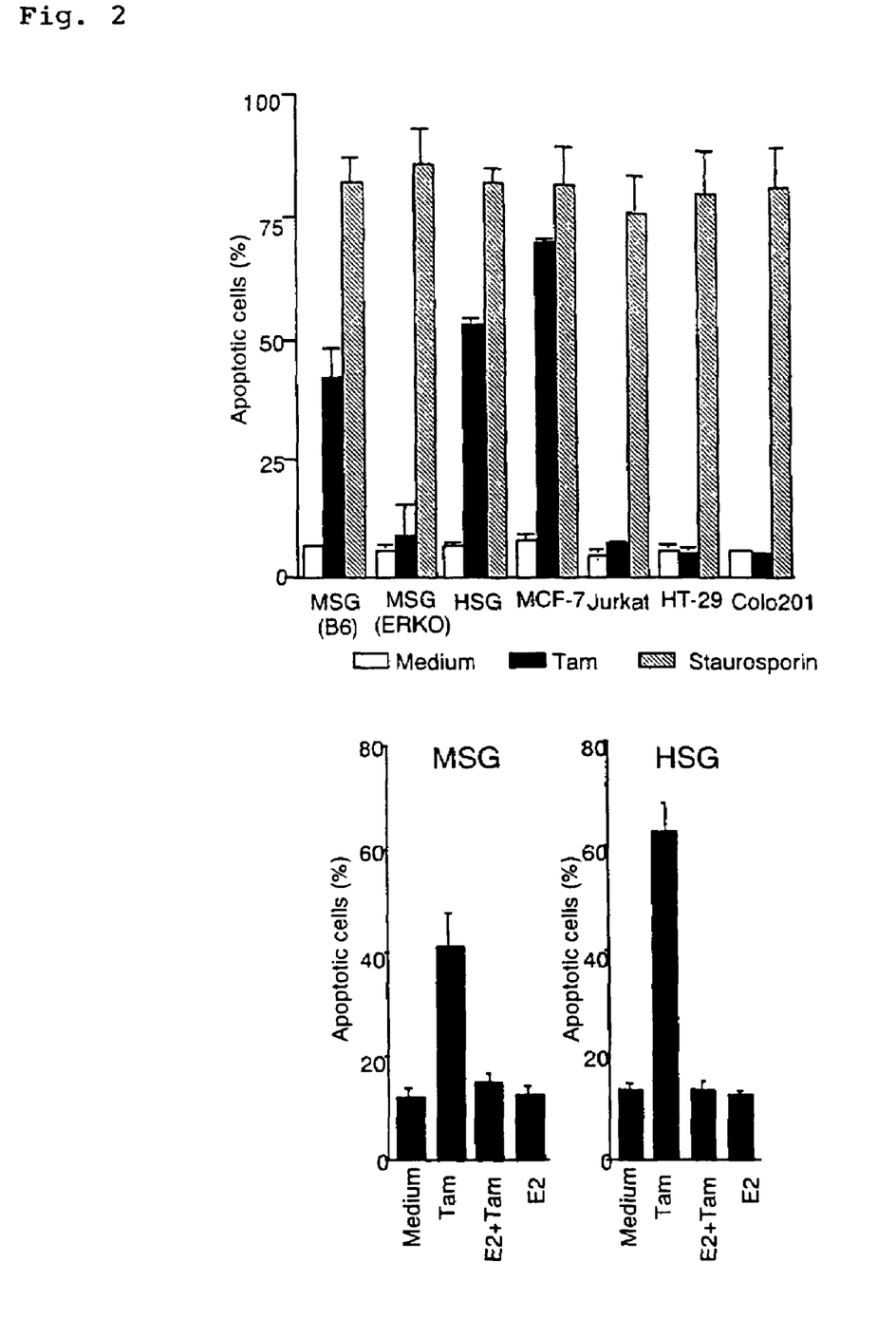
FIG. 2 is a graph showing apoptosis induction in cultured cells, wherein "apoptotic cells" represents the percent apoptotic cells, "Medium" represents control groups, "Tam" represents groups to which tamoxifen had been added, "Staurosporin" represents groups to which staurosporin had been added, "E2" represents groups to which estradiol had been added, and "E2+Tam" represents groups to which estradiol and tamoxifen had been added.

Cells of each of the following cell lines were cultured through a routine method; mouse salivary gland cell lines (MSG:B6 and ERαKO); human salivary gland cell line (HSG); human breast cancer cultured-cell line (MCF-7); human acute T cell leukemia cell line (Jurkat); and human colon cancer cultured-cell lines (HT-29 and Colo201). The cultured cells were reacted with tamoxifen (Tam, final concentration: $10^{-7}$ M), an antagonist of estrogen. The resultant cells were observed in terms of Tam's effect on apoptosis and saliva-gland-specific antigens, and activity of apoptosis-related proteases (e.g., caspase) was investigated. Separately, the above cultured cells were reacted with staurosporin (an apoptosis inducer, final concentration: $10^{-6}$ M), and the resultant cells were used as a positive control group. Forty-eight hours after the addition of Tam, apoptosis of the cells was determined by means of a flow cytometer, by use of Annexin-V-FITC. As a result, as shown in FIG. 2, the percent apoptotic cells of the MSG cell (B6) group or the HSG cell group was found to be significantly high as compared with those of the groups to which Tam had not been added. Notably, apoptosis of MCF-7 had been known to be induced by Tam. Apoptosis of the ERαKO-mouse-derived MSG cells was found not to be induced by Tam. In addition, the percent apoptotic cells of the staurosporin-added groups was found to be high and not to differ from one group to another. Moreover, when the salivary gland cells had been pretreated with estradiol (E2, final concentration: $10^{-9}$ M, addition time: twenty-four hours before stimulation by Tam), apoptosis of the cells induced by Tam was found to be suppressed, indicating that estrogen participates in apoptosis of the salivary gland cells induced by Tam.

Example 3

Figure 3:
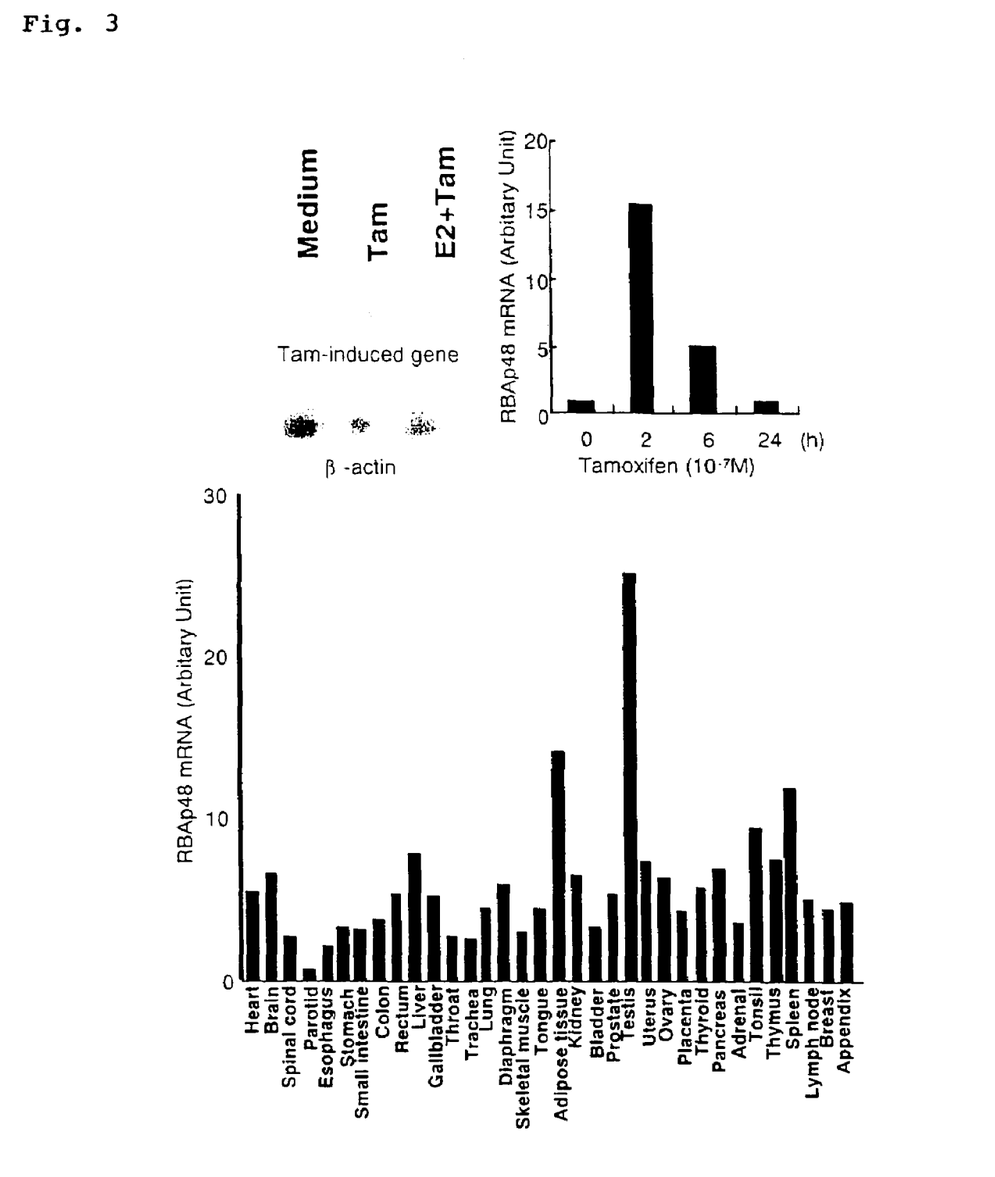
FIG. 3 shows genes which exhibits enhanced expression by anti-estrogen effect, wherein "Medium" represents a control group, "Tam" represents a group to which tamoxifen had been added, and "E2+Tam" represents a group to which estradiol and tamoxifen had been added.

Identification of the Genes which Exhibit Enhanced Expression by Anti-estrogen Effect HSG cells were stimulated by Tam to thereby cause expression of mRNAs. mRNAs which exhibited enhanced expression as compared with those of non-stimulated HSG cells were extracted through a routine method and isolated through the differential display method (RNA image kit, Gene Hunter™, Toyobo). The thus-obtained DNA fragments were transferred into E. Coli for cloning. The thus-obtained mRNAs were investigated through northern blotting (FIG. 3) by use of HSG cells and the isolated DNA fragments serving as probes, to thereby determine mRNAs which exhibit enhanced expression by tamoxifen (final concentration: $10^{-7}$ M), and the expression was reduced by addition of estradiol (final concentration: $10^{-9}$ M). The amino acid sequences of the DNA fragments were determined through a routine sequencing method. The DNA fragments were identified to be the RBAp48 gene. Two hours after Tam stimulation, the HSG cells were found to exhibit strong RBAp48 mRNA expression. Moreover, RBAp48 was expressed through use of each of human normal organ mRNAs, and the expressed RBAp48 was investigated through northern blotting. RBAp48 was found to exhibit the greatest reduction in expression in salivary gland tissues and strong expression in testis tissues and adipose tissues among the investigated human organ tissues. These results indicate that RBAp48, which exhibits reduced expression in normal salivary gland cells, may exhibit increased expression by anti-estrogen effect.

Example 4

Figure 4:
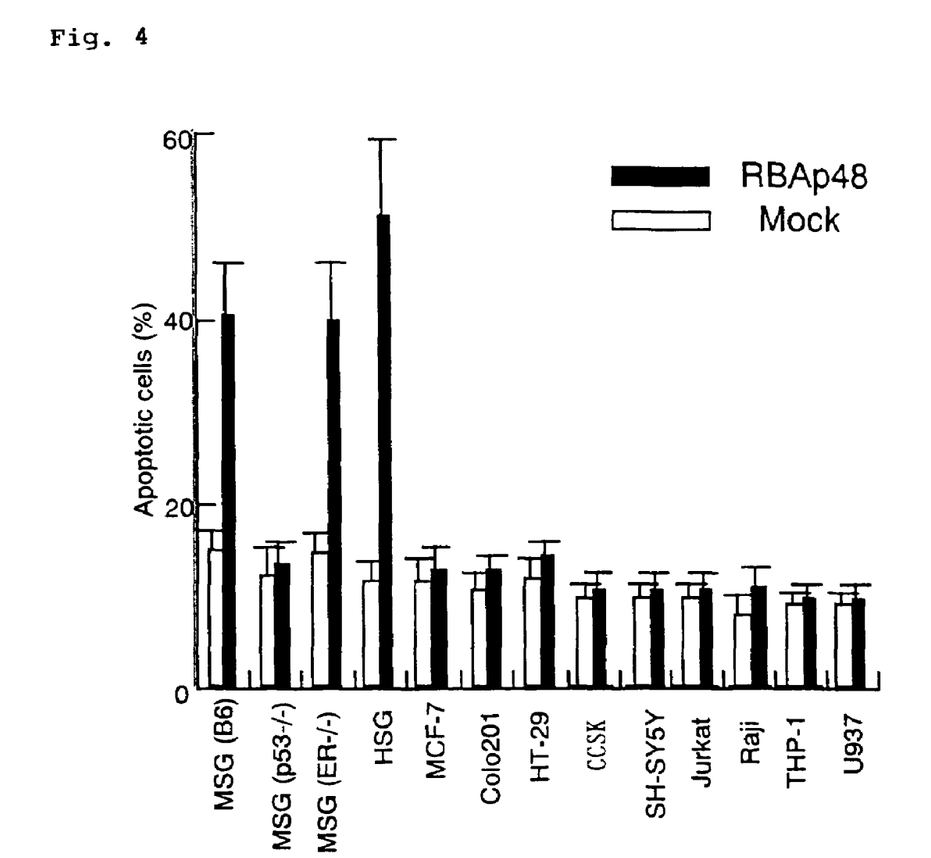
FIG. 4 is a graph showing apoptosis of cells of various cell lines caused by transferring RBAp48 gene to the cells, wherein "apoptotic cells" represents the percent apoptotic cells.

Investigation of Apoptosis by Transferring RBAp48 Genes into Cells of Various Cell Lines In order to elucidate functions of RBAp48 in salivary gland cells, RBAp48 genes (final level: 1 μg/mL) which had been inserted into pCMV vectors were transferred through lipofectin into cells of various cell lines (the cell lines employed in the above Tam stimulation, CCSK: human cholangiocarcinoma cell line, SH-SY5Y: human nerve cell line, Raji:

human B cell line, THP-1, U937: human monocytic leukemia cell line). Forty-eight hours after the transfer, the percent apoptotic cells of each cell group was determined by means of a flow cytometer, by use of Annexin-V-FITC. As a result, the percent apoptotic cells of the B6-mouse-derived MSG cell group, the ERαKO-mouse-derived MSG cell group, and the HSG cell group were found to be significantly high as compared with those of the Mock groups (vector only), and the p53KO-mouse-derived MSG cell group and other cell groups were found not to exhibit apoptosis induced by RBAp48 overexpression (FIG. 4). These results indicate that apoptosis caused by RBAp48 expression is induced specifically in the salivary gland cells, that such apoptosis involves estrogen receptor and the downstream signals thereof, and that p53 molecules play a key role in such apoptosis.

Example 5

Establishment of RBAp48-stable Cell Line and Study of Apoptosis Route

Figure 5:
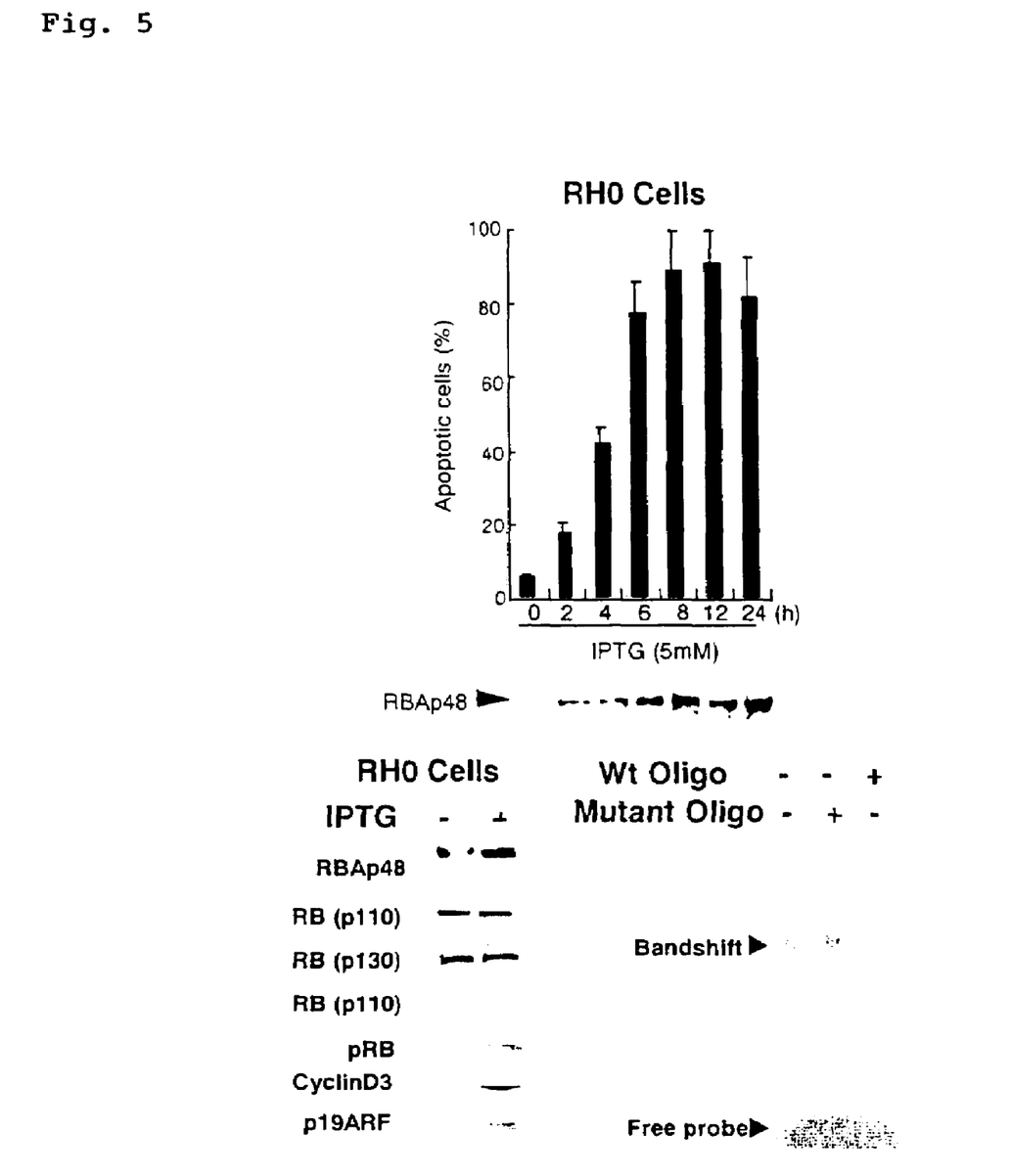
FIG. 5 shows apoptosis of cells of the RBAp48-stable cell line, wherein "apoptotic cells" represents the percent apoptotic cells, and "IPTG" represents isopropyl-β-D-thiogalactoside.

A stable cell line in which RBAp48 expression is stably regulated by addition of IPTG to the culture system is established by means of LacSwitch II Inducible Mammalian Expression System (STRATEGENE) through use of HSG cells (RHO cell). As shown in FIG. 5, the percent apoptotic cells was found to increase over time from two hours to twelve hours after addition of IPTG, and RBAp48 protein expression was found to increase in accordance with increase in the apoptotic cells. Separately, the RHO cells were investigated in terms of cell cycle related molecules (i.e., RBs, phosphorylated RB, CyclinD3, and p19ARF) in the cell lysates six hours after addition of IPTG, through western blotting by use of the corresponding antibodies (BD Transduction Laboratory). As a result, addition of IPTG was found to cause no change in expression of RB proteins but to cause enhanced expression of RB phosphorylation, cyclinD3, and p19ARF. In addition, a nuclear extract of IPTG-added RHO cells was subjected to gel shift assay. The transcription activity of E2F-1 was found to be high (FIG. 5).

Example 6

Figure 6:
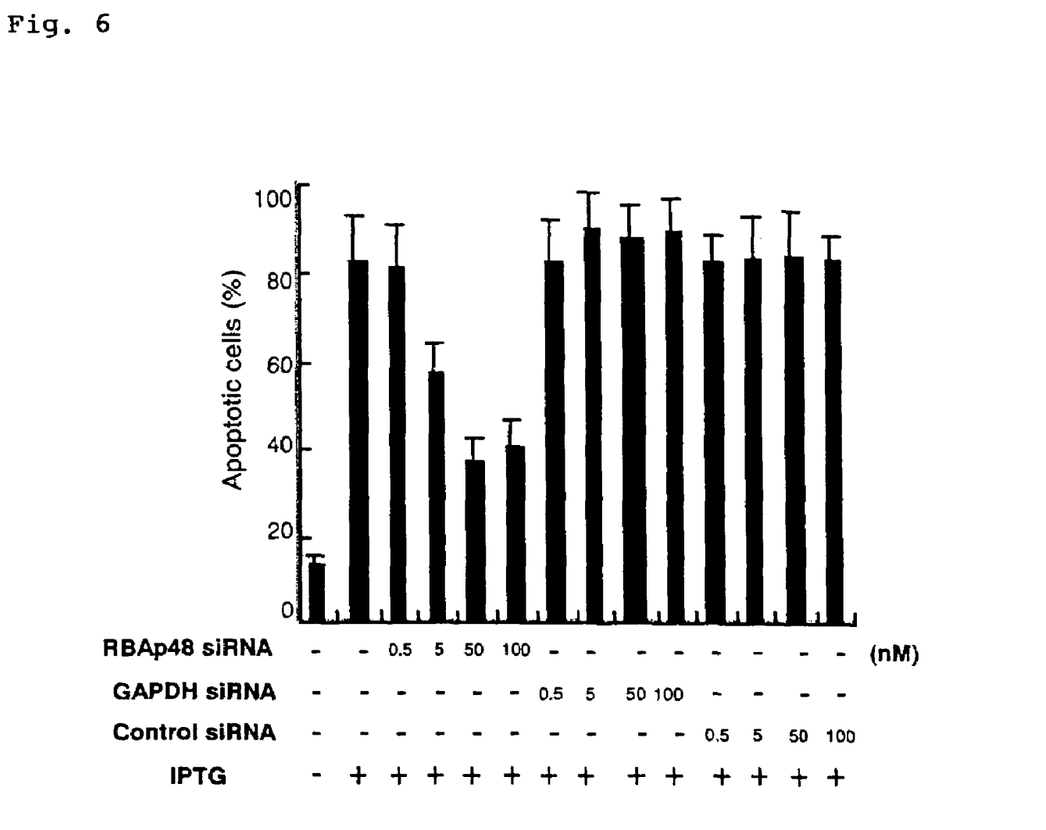
FIG. 6 shows effect of RBAp48 siRNA on RBAp48-induced apoptosis, wherein "apoptotic cells" represents the percent apoptotic cells.

Effect of RBAp48 siRNA on RBAp48-induced Apoptosis siRNA of RBAp48 was prepared (sense; CGA GGA AUA CAA AAU AUG GTT (SEQ ID NO: 1), antisense; CCA UAU UCU GUA UUC CUC GTT (SEQ ID NO: 2)). The siRNA was transferred into cells of the RBAp48-stable cell line, and whether the siRNA exhibits an effect on apoptosis involving RBAp48 was investigated. As shown in FIG. 6, RBAp48 siRNA (final level: 0.5 to 100 nM) was transferred into RHO cells through lipofection, and IPTG was added to the cells twenty-four hours after the transfer, followed by culture for eight hours. The percent apoptotic cells of the cultured cells was determined by means of a flow cytometer, by use of Annexin-V-FITC. Apoptosis induced by addition of IPTG was found to be significantly suppressed by transfer of 50 nM RBAp48 siRNA. In contrast, GAPDH siRNA or non-functional control siRNA was found not to exhibit any effect on apoptosis of salivary gland cells induced by addition of IPTG.

All the above results reveal that RBAp48 strongly participates in molecular mechanism of onset of autoimmune diseases, which are frequently found in menopausal women, and that a novel therapeutic method for autoimmune diseases can be developed by using apoptosis inhibition of the target cells. If inhibition of RBAp48 expression is clinically applied in treatment of intractable diseases, a great contribution to the society would be provided.

The present invention provides a method for treating autoimmune diseases, for which radical therapies have not yet been obtained, a screening method for preventive or therapeutic agents for autoimmune diseases, and a diagnostic method for autoimmune diseases. The content of Japanese Patent Application No. 2003-123959 is hereby incorporated by reference in its entirety.

What is claimed is:

1. A method for diagnosing Sjögren's syndrome in a subject, comprising measuring the level of retinoblastoma associated protein 48 (RBAp48) in salivary gland tissue or lacrimal gland tissue from said subject and correlating an increase in the level of RBAp48 in said gland tissue with a diagnosis of Sjögren's syndrome.

2. The method according to claim 1, wherein the RBAp48 level is a RBAp48 protein level or RBAp48 gene expression level.

3. The method according to claim 1, wherein the RBAp48 level is determined through an immunological assay.

4. The method according to claim 1, wherein the RBAp48 level is the gene expression level and the gene expression level is determined by an assay selected from the group consisting of PCR assay, northern blotting assay, or microarray.

* * * * *

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 1
cgaggaauua caaaacaugg tt                                              22

<210> SEQ ID NO 2
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 2
ccauauucug uauuccucgt                                                 20
```